(12) United States Patent
Miyahara et al.

(10) Patent No.: US 12,076,061 B2
(45) Date of Patent: *Sep. 3, 2024

(54) BONE NAIL

(71) Applicant: Arthrex Trauma, Inc., Naples, FL (US)

(72) Inventors: Kazunori Miyahara, Long Beach, CA (US); Kenneth J Koval, Orlando, FL (US); Joshua R Langford, Orlando, FL (US)

(73) Assignee: Arthrex Trauma, Inc., Naples, FL (US)

( * ) Notice: Subject to any disclaimer, the term of this patent is extended or adjusted under 35 U.S.C. 154(b) by 508 days.

This patent is subject to a terminal disclaimer.

(21) Appl. No.: 17/167,899

(22) Filed: Feb. 4, 2021

(65) Prior Publication Data

US 2021/0153917 A1    May 27, 2021

Related U.S. Application Data

(63) Continuation of application No. 16/258,001, filed on Jan. 25, 2019, now Pat. No. 10,932,828.

(60) Provisional application No. 62/622,084, filed on Jan. 25, 2018.

(51) Int. Cl.
| | | |
|---|---|---|
| A61B 17/72 | (2006.01) | |
| A61B 17/17 | (2006.01) | |
| A61B 17/74 | (2006.01) | |
| A61B 17/16 | (2006.01) | |
| A61B 17/80 | (2006.01) | |
| A61B 17/86 | (2006.01) | |

(52) U.S. Cl.
CPC .......... *A61B 17/72* (2013.01); *A61B 17/1725* (2013.01); *A61B 17/744* (2013.01); *A61B 17/1664* (2013.01); *A61B 17/1717* (2013.01); *A61B 17/1721* (2013.01); *A61B 17/8061* (2013.01); *A61B 17/86* (2013.01)

(58) Field of Classification Search
CPC ........................................... A61B 17/72–7291
See application file for complete search history.

(56) References Cited

U.S. PATENT DOCUMENTS

| | | |
|---|---|---|
| 5,034,013 A | 7/1991 | Bryant et al. |
| 5,112,333 A | 5/1992 | Fixel |
| 5,374,235 A | 12/1994 | Ahrens |
| 5,429,640 A | 7/1995 | Latour, Jr. et al. |
| 5,472,444 A | 12/1995 | Conrad et al. |
| 5,620,445 A | 4/1997 | Brosnahan et al. |
| 5,776,194 A | 7/1998 | Chambers et al. |
| 5,814,047 A | 9/1998 | Emilio et al. |
| 5,971,986 A * | 10/1999 | Santori .............. A61B 17/7266 606/62 |
| 6,123,708 A | 9/2000 | Davenport et al. |

(Continued)

*Primary Examiner* — Eduardo C Robert
*Assistant Examiner* — Michelle C Eckman
(74) *Attorney, Agent, or Firm* — Carlson, Gaskey & Olds, P.C.

(57) ABSTRACT

A bone nail for stabilizing a fracture. The bone nail having a head portion and a stem portion. The stem portion offset from the longitudinal axis of the head portion. The nail including a continuous passageway extending from a rear edge of the nail to a front edge of the nail. The continuous passageway including a bore extending longitudinally through the head portion and both a groove and a bore in the stem portion.

8 Claims, 8 Drawing Sheets

(56) References Cited

U.S. PATENT DOCUMENTS

| | | | |
|---|---|---|---|
| 6,126,661 A | 10/2000 | Faccioli et al. | |
| 6,228,086 B1 | 5/2001 | Wahl et al. | |
| 6,296,645 B1 | 10/2001 | Hover et al. | |
| 6,527,775 B1 | 3/2003 | Warburton | |
| 6,547,791 B1 | 4/2003 | Bernhard et al. | |
| 9,788,871 B2 * | 10/2017 | Simon | A61B 17/8897 |
| 10,932,828 B2 * | 3/2021 | Miyahara | A61B 17/744 |
| 2001/0053912 A1 | 12/2001 | Frigg | |
| 2002/0103488 A1 | 8/2002 | Lower | |
| 2002/0143337 A1 | 10/2002 | Orbay | |
| 2002/0173792 A1 * | 11/2002 | Severns | A61B 17/72 606/62 |
| 2003/0069581 A1 | 4/2003 | Stinson | |
| 2004/0172027 A1 | 9/2004 | Speitling | |
| 2005/0055023 A1 | 3/2005 | Sohngen | |
| 2005/0075637 A1 | 4/2005 | Semet | |
| 2006/0149257 A1 | 7/2006 | Orbay | |
| 2006/0161155 A1 | 7/2006 | Schlienger | |
| 2006/0161156 A1 | 7/2006 | Orbay | |
| 2006/0200142 A1 | 9/2006 | Sohngen | |
| 2006/0200160 A1 | 9/2006 | Border | |
| 2007/0100343 A1 | 5/2007 | Barker et al. | |
| 2007/0123878 A1 | 5/2007 | Shaver | |
| 2007/0270845 A1 | 11/2007 | Watanabe | |
| 2007/0299447 A1 * | 12/2007 | Watanabe | A61B 17/164 606/62 |
| 2008/0140077 A1 | 6/2008 | Kebaish | |
| 2008/0183171 A1 | 7/2008 | Elghazaly | |
| 2008/0262496 A1 | 10/2008 | Schlienger | |
| 2008/0287951 A1 | 11/2008 | Stoneburner | |
| 2008/0287958 A1 | 11/2008 | Logan | |
| 2008/0312702 A1 | 12/2008 | Schlienger | |
| 2009/0048600 A1 | 2/2009 | Matityahu | |
| 2009/0326534 A1 | 12/2009 | Yamazaki | |
| 2010/0256638 A1 | 10/2010 | Tyber | |
| 2010/0256639 A1 | 10/2010 | Tyber | |
| 2010/0324556 A1 | 12/2010 | Tyber | |
| 2011/0087227 A1 | 4/2011 | Mazur | |
| 2011/0172667 A1 | 7/2011 | Richards | |
| 2011/0282347 A1 | 11/2011 | Gordon | |
| 2011/0295254 A1 | 12/2011 | Brunnarius | |
| 2012/0059376 A1 | 3/2012 | Rains | |
| 2012/0197255 A1 | 8/2012 | Elghazaly | |
| 2013/0053847 A1 | 2/2013 | Siravo | |
| 2013/0131679 A1 | 5/2013 | Janna | |
| 2013/0150851 A1 * | 6/2013 | Nardini | A61B 17/7233 606/64 |
| 2013/0172890 A1 | 7/2013 | Limouze | |
| 2013/0204251 A1 | 8/2013 | Appenzeller | |
| 2013/0274745 A1 | 10/2013 | Kmiec, Jr. | |
| 2013/0325006 A1 | 12/2013 | Michelinie | |
| 2014/0058392 A1 | 2/2014 | Mueckter | |
| 2014/0066932 A1 | 3/2014 | Appenzeller | |
| 2014/0135769 A1 | 5/2014 | Ziran | |
| 2014/0142575 A1 | 5/2014 | Biedermann | |
| 2014/0296853 A1 | 10/2014 | Wolter | |
| 2014/0296854 A1 | 10/2014 | Wolter | |
| 2015/0032110 A1 | 1/2015 | Boraiah | |
| 2015/0112345 A1 | 4/2015 | Boraiah | |
| 2015/0305791 A1 | 10/2015 | Purohit | |
| 2017/0105776 A1 | 4/2017 | Lutz | |
| 2017/0296241 A1 | 10/2017 | Garlock | |
| 2018/0028241 A1 | 2/2018 | Levy | |
| 2018/0042651 A1 | 2/2018 | Little | |
| 2018/0078292 A1 | 3/2018 | Hedgeland | |
| 2018/0177537 A1 | 6/2018 | Van Dyke | |
| 2018/0344377 A1 | 12/2018 | McManus | |
| 2019/0038326 A1 | 2/2019 | Hedgeland | |
| 2019/0105086 A1 | 4/2019 | Janda | |
| 2019/0105087 A1 | 4/2019 | Sommers | |
| 2019/0117282 A1 | 4/2019 | Singh | |
| 2019/0175232 A1 | 6/2019 | Karg | |
| 2019/0216513 A1 | 7/2019 | Sands | |
| 2019/0223925 A1 | 7/2019 | Miyahara | |
| 2019/0274742 A1 | 9/2019 | Garlock | |
| 2019/0282279 A1 | 9/2019 | Rains | |
| 2019/0314065 A1 | 10/2019 | Petersik | |

* cited by examiner

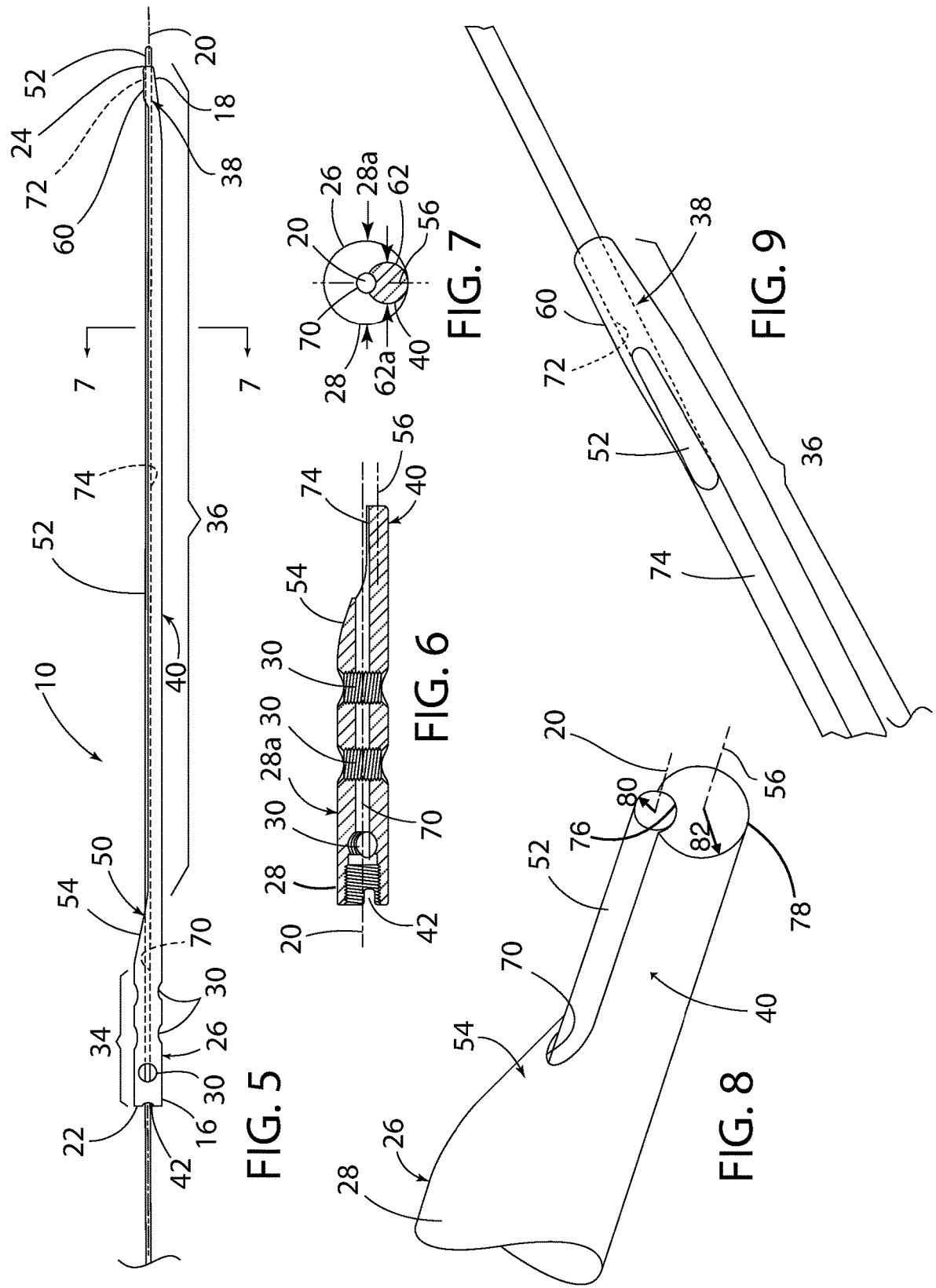

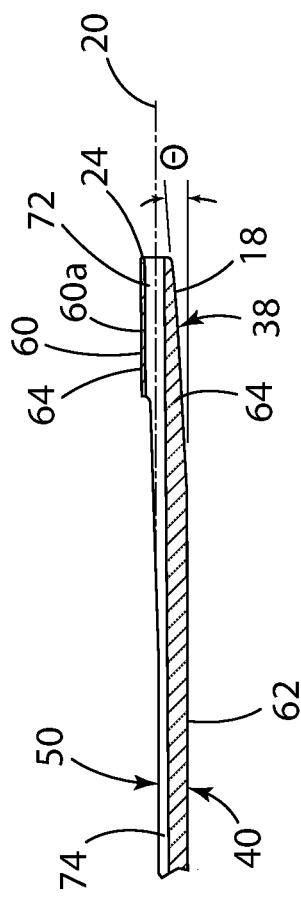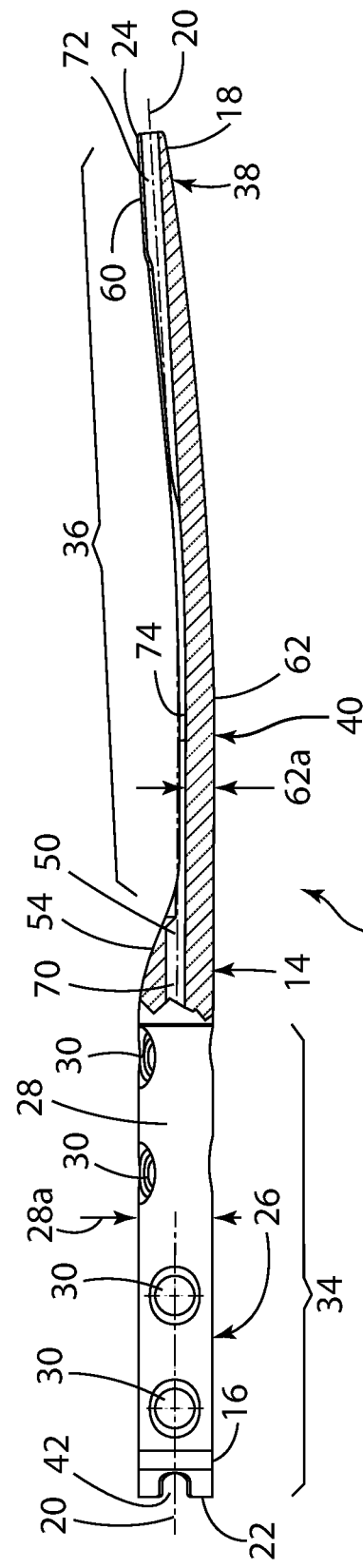

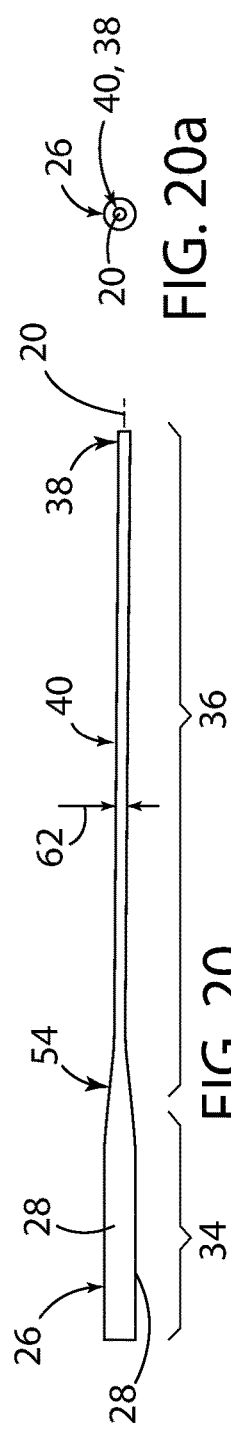

BONE NAIL

CROSS-REFERENCE TO RELATED APPLICATIONS

This application is a continuation of U.S. patent application Ser. No. 16/258,001, filed Jan. 25, 2019, which claims the benefit of U.S. Provisional Application No. 62/622,084, filed Jan. 25, 2018. The disclosure of the forgoing applications is incorporated herein by reference.

BACKGROUND OF THE INVENTION

1. Field of the Invention

The present invention generally relates to an orthopedic fixation device; and more specifically, to a nail for treating a bone fracture.

2. Description of Related Art

Orthopedic fixation devices used for stabilizing a fracture often include an elongated implant such as a nail or pin inserted into a medullary canal of the bone to stabilize the fracture and promote healing. Often referred to as an intramedullary nail, such devices are used with large or long bones, such as a femur, tibia, or humerus.

Intramedullary nails stabilize a fracture until the fracture heals. The intramedullary nail is inserted in the medullary canal of the bone and positioned to span the fracture. Bone screws placed through aligned apertures in the nail are received in, and anchor the nail within, the bone. The screws are usually inserted in a proximal end of the nail. In addition, the distal end of the nail may also receive a screw. The orientation of the screws depends upon the fracture configuration and the type of large or long bone fracture.

Fractures of smaller bones, for example, a fibula, are often treated using a plate-and-screw fixation device, often called a bone plate. Plate-and-screw devices typically include a flat metallic plate covering a significant part of the outer bone surface or bone cortex and affixed thereto. Because bone plates contact the bone surface, they can lessen the amount of blood, and correspondingly the oxygen and other bone nutrients contained therein, that flows over the bone, especially around the fracture. This situation may delay the healing of the fracture, and impair the overall health of the bone itself.

Intramedullary nails may offer distinct advantages. For example, intramedullary nails may help bones heal faster, with lower rates of infection as compared to other surgical methods of fixation. Achieving improved early mobilization of limbs having the broken bone is another advantage. A significant improvement over other methods of fixation is that intramedullary nails may share loads with the bone, rather than entirely supporting the bone across the fracture site. Because of this, patients may move the broken limb sooner than they would with traditional casting of the bone. This may help maintain more strength of the muscles and prevent frozen joints, joints that become stiff after prolonged casting.

SUMMARY OF THE INVENTION

A bone nail for treating a fracture. The bone nail having a head portion and a stem portion. The stem portion including a distal portion bent at an angle relative to a longitudinal axis of the stem portion. The nail having a continuous passageway extending between a rear edge and a front edge, the passageway including a bore in the head portion, a groove through at least a portion of the stem portion, and a bore in the distal portion.

In one embodiment, the bone nail includes a proximal portion; a distal portion; and a medial portion. A bore extends through the proximal portion and the distal portion but not through the medial portion.

Further areas of applicability of the present invention will become apparent from the detailed description provided. It should be understood that the detailed description and specific examples, while indicating the preferred embodiment of the invention, are intended for purposes of illustration only and are not intended to limit the scope of the invention.

BRIEF DESCRIPTION OF THE DRAWINGS

The present invention will become more fully understood from the detailed description and the accompanying drawings, wherein:

FIG. 5 is a side view of an embodiment of a nail according to the present invention.

FIG. 6 is a partial cross-sectional view of the nail of FIG. 5.

FIG. 7 is an end view of the nail of FIG. 5 taken from the right side of FIG. 5.

FIGS. 8 and 9 are partial perspective views showing various aspects of the nail of FIG. 5.

FIG. 10 is a partial cross-sectional view of a portion of the nail of FIG. 5 including a distal portion.

FIGS. 11-13 are a partial cross-sectional side view, top view, and bottom view of an embodiment of the nail according to the present invention.

FIGS. 20-24a are schematic side and end views of a manufacturing process for making a nail according to the present invention.

DETAILED DESCRIPTION OF THE PREFERRED EMBODIMENTS

The following description of the preferred embodiment(s) is merely exemplary in nature and is in no way intended to limit the invention, its application, or uses.

Unless otherwise noted, as used in this specification and the appended claims, the terms "top," "bottom," "side," "end," "left," "right," and/or the like, are used herein solely for reference purposes and are not meant to limit the scope of the present invention.

When used to identify a portion or end of a bone, "proximal" refers to something closer to the torso while "distal" refers to parts and places away from the torso. In addition, the term "at" when referring to the location or placement of an element or object means in, near or by the area or location occupied by the structure or element referred to.

The longitudinal axis is a direction of orientation, along a lengthwise direction of the body or element.

Figure 1:
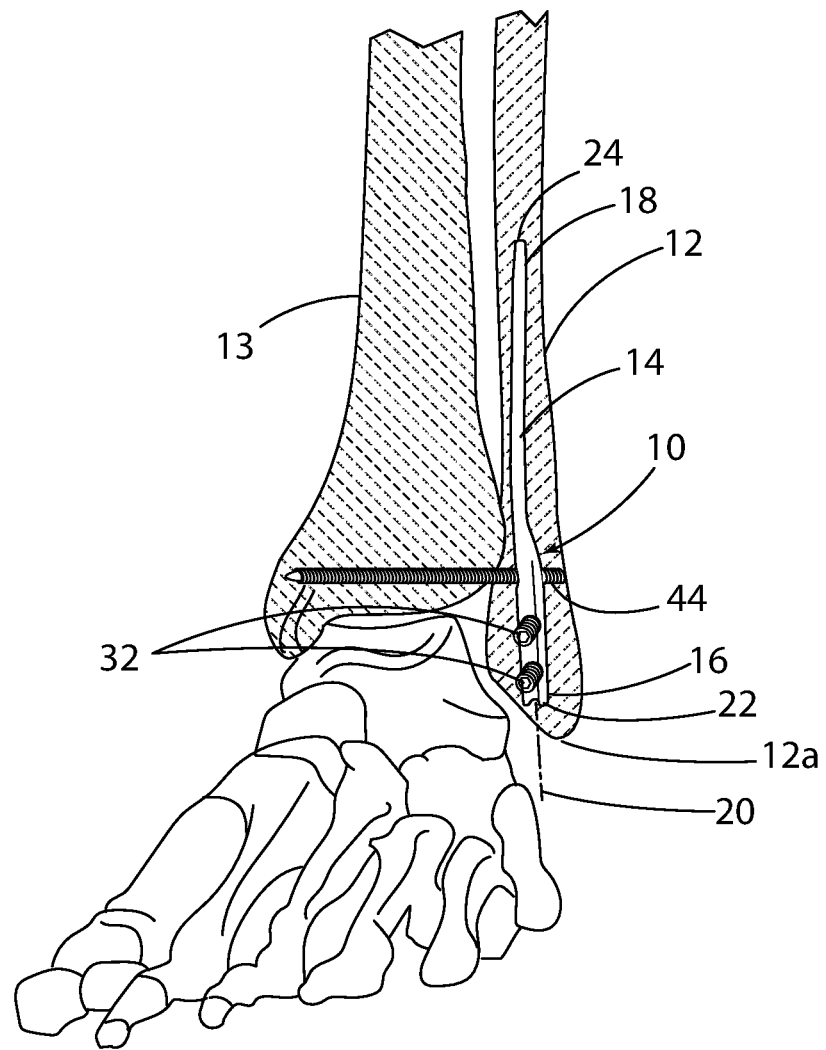
FIG. 1 is a schematic perspective view of a nail in a fibula in accordance with the principles of the present disclosure.

FIG. 1 shows a bone nail or intramedullary nail 10 according to an embodiment of the present invention placed in an assembled condition within a bone 12; specifically, an antegrade insertion in a fibula. The term "nail" as used here refers to a connective orthopedic implant, including but not limited to a nail for use in a fibula, and any other connective implant device suitable for use in any bone of interest, for example, the ulna and radius. The nail 10 is typically inserted into the medullary cavity or marrow canal of a fibula. The nail 10 may be referred to as an intramedullary nail because it is situated or placed within a medulla and uses the marrow space of a bone; intramedullary means the inside of a bone.

The nail 10 may be useful in other types of bones in addition to fibulas, in accordance with the principles of the present disclosure. While shown herein extending only partially along the length of the fibula, an embodiment of the present disclosure may include the nail 10 configured to extend substantially an entire length of the bone. For example, the phrase "substantial entire length" of a bone means approximately seventy-five percent of the length of the bone or more. Other embodiments of the nail may be configured to extend different lengths with respect to the bone.

FIG. 1 illustrates one configuration for fastening or connecting the head portion 34, including the proximal portion 26, of the nail 10 to the bone 12, as shown, the fibula. Anterior-to-posterior (AP) screws or anchor members 32 extend through the apertures or transverse bores 30 and into the fibula. In addition, a syndesmotic screw 44, for example, a screw designed to replace the syndesmosis of the human body, usually temporarily, extends through an aperture or transverse bore 30 and into the tibia. As known, a syndesmotic screw may replace the inferior tibiofibular articulation and fix the tibia and fibula together at the lower joint.

Figure 4:
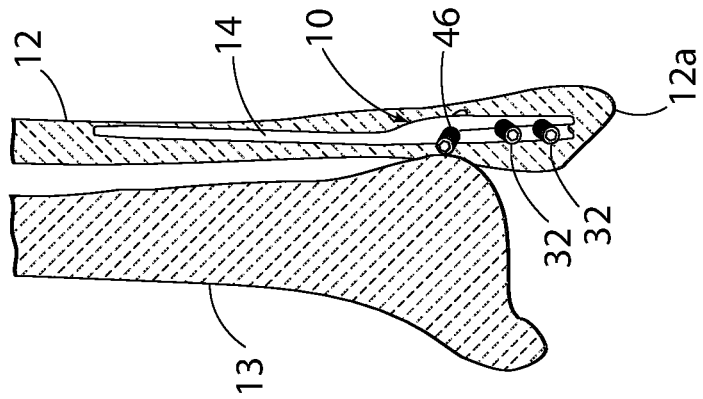
FIGS. 2-4 are schematic perspective views of different embodiments of a nail in a fibula in accordance with principles of the present disclosure.
Figure 3:
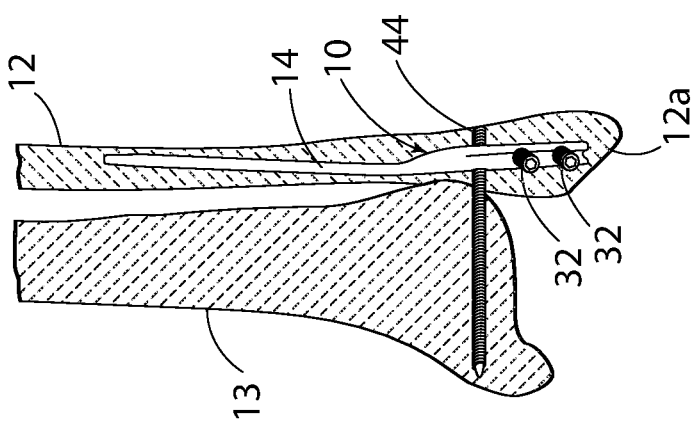
Figure 2:
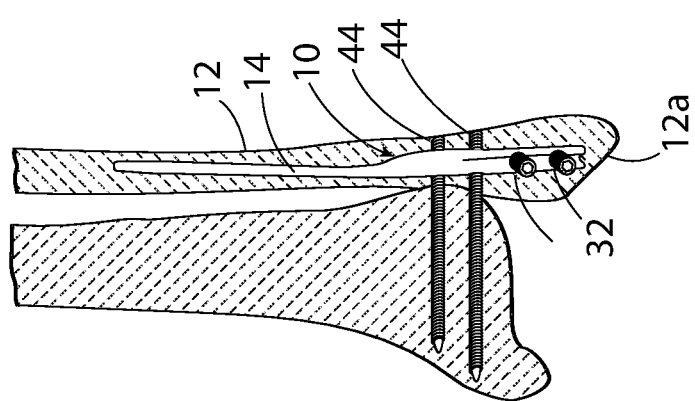

FIGS. 2-4 illustrate different fastening configurations for fastening or connecting the nail 10, that is fixing the nail 10 in position to stabilize a fracture of the fibula 12. FIG. 2 illustrates the use of two anterior-to-posterior (AP) screws or anchor members 32 received in the fibula 12 and two syndesmotic screws 44 extending through the fibula and received in the tibia 13. FIG. 3 illustrates the use of two anterior-to-posterior (AP) screws or anchor members 32 received in the fibula 12 and one syndesmotic screws 44 extending through the fibula and received in the tibia 13. FIG. 4 illustrates the use of two anterior-to-posterior (AP) screws or anchor members 32 received in the fibula 12 and one oblique screw 46 also received in the fibula 12, wherein no syndesmotic screws 44 are received in the tibia 13.

As illustrated in FIGS. 5-10, the nail 10 includes an elongated body or member 14 formed of a metallic alloy, such as a titanium alloy. The elongated body 14 having a proximal end 16, a distal end 18, and a longitudinal axis 20 extending between the proximal end 16 and the distal end 18. The proximal end 16 having a trailing or rear edge 22 and the distal end 18 having a leading or front edge 24. The respective rear and front edges being the transition between the location or transition from a longitudinal outer surface of the nail 10. The terms leading/front and trailing/rear referring to the direction or orientation of insertion of the nail 10. When referring the "proximal" and "distal" ends or portions of the nail, the term "proximal" refers to that end or portion of the nail 10 typically placed at, adjacent or near an end of the bone 12, while "distal" refers to that end or portion of the nail 10 typically extending further into the bone 12, that is inwards from the end of the bone towards the center or medial portion thereof. For example, in the disclosed example, the nail 10 is designed for retrograde insertion into the intramedullary canal of the fibula 12. As shown in FIGS. 1-4, the proximal end 16 of the intramedullary nail 10 is located adjacent the distal end 12a of the bone 12. This position referred to as retrograde nailing wherein the proximal end 16 of the nail 10 is fixed in the distal end 12a of the bone 12. As illustrated, the distal end 18 of the nail 10 is closer to the opposite end (not shown) of the bone 12 than the proximal end 16 of the nail 10. In contrast, antegrade nailing fixes the proximal end 16 of the nail 10 in the proximal end of the bone.

The elongated body includes a proximal portion or section 26 formed of a generally cylindrical configuration having an outer circumferential surface 28 and an outer diameter 28a, a straight line passing from side to side through the center of a body or figure, here the proximal portion. The proximal portion or section 26 including at least one and, in the disclosed embodiment, multiple openings or transverse bores 30. The openings 30 extend through the proximal portion or section 26 and across the longitudinal axis 20 and receive anchor members 32, such as bone screws, to anchor the nail 10 in the bone 12. The openings 30 extend across the longitudinal axis 20 at an angle of 90° or less.

The anchor members 32, such as bone screws, received in the transverse bores 30 anchor the proximal portion or section 26 and correspondingly the proximal end 16 of the elongated body 14 within the distal end 12a of the bone 12. The anchor members 30 may be bone screws or any other suitable variety of fastening mechanism known in the art for use with intramedullary nails. The shape, size, and configuration of the anchor members 30 may vary within the scope of the present disclosure.

In an exemplary embodiment, the elongated body 14 of the nail 10 includes a head portion 34 and a stem portion 36. The head portion 34 including the proximal portion or section 26 at the proximal end 16. The stem portion 36 including a distal portion or section 38 at the distal end 18. FIG. 7 shows the outer diameter of the head portion 34, the outer diameter 28a of proximal end 26, being greater than the outer diameter 62a of the outer surface 62 of the stem portion 36. The stem portion may also include the distal portion 38 having or including a conical tip 60 in at the distal end 18. In the disclosed embodiment, the stem portion or section 34 includes the distal portion 38 and distal end 18. The shape or configuration of the stem portion or section 34 may vary between the proximal portion or section 26 and the leading or front edge 24 of the distal end 18. The nail 10 includes a passageway, seen generally at 50, that extends longitudinally through the nail member 10 between the trailing or rear edge 22 of the proximal end 16 and the leading or front edge 24 of the distal end 18. Passageway, as used herein, is a way, typically having a wall(s); for example, a bore, duct, tube, canal, groove, path, channel, conduit, or similar structure. The passageway configured to receive a guide wire 52 used for inserting the nail 10. The passageway 50 provides a longitudinal path for inserting the nail 10 over a guide wire 52 as shown in FIGS. 5-9.

In an exemplary embodiment, the elongated body 14 includes an intermediate, central, or medial portion or section 40 extending or lying between the proximal portion or section 26 at the proximal end 16 and the distal portion or section 38 at the distal end 18. The nail 10 may be viewed as including three areas or regions, a proximal portion 26, a medial portion 40 and a distal portion 38. The distal portion 38 is that part of the nail 10 located nearby or adjacent to the distal end 18. As explained subsequently, the distal portion 38 being that portion of the nail 10 including the bore or aperture 72. It may also include a bend in the stem portion 36, see FIG. 10 with the bend offset or extending at an angle θ with respect to the longitudinal axis 20, wherein a portion of the outer surface 62 of the medial portion 40 extends parallel to the longitudinal axis 20.

The proximal portion 26 is that part of the nail 10 located nearby or adjacent to the proximal end 16 and including the bore or aperture 70. The medial portion 40 is that area of the nail 10 between the proximal and distal portions 26, 38 and including the groove 74. Typically, the stem portion 36 encompasses the medial portion 40 and distal portion 38, with the head portion 34 in the proximal portion 26. The size or length of the respective areas in relation to one another may vary depending upon the overall length of the elongated body 14 of the nail 10. When the nail 10 is used in a small bone such as the fibula, the medial portion occupies more than one-half (½) of the overall length of the elongated body 14 of the nail 10 and in some instances more than three quarters (¾) of the overall length of the elongated body 14.

A fitting, shown as slot 42, may be disposed on the head portion 34 at the trailing or rear edge 22 of the proximal end 26. The fitting 42 configured for receiving a tool (not shown) for manipulating the nail 10, or for attaching an alignment guide or jig.

A transition portion 54 extends between the intermediate or medial portion 40 and the proximal portion or section 26. The transition portion 54 may include a tapered portion extending inwardly from the outer surface 28 of the proximal portion or section 26 to the outer surface of the intermediate or medial portion 40. As illustrated, past the transition portion 54, at least part of the intermediate portion 40 is offset from the longitudinal axis 20 of the nail 10. In the exemplary embodiment, the proximal portion or section 26 is a longitudinally extending cylindrical member having a circular cross section. The intermediate portion 40 has a crescent shaped cross section and is defined by a first arc 76 having a first radius 80 and a second arc 78 having a second radius 82 different than the first radius 80. The crescent shape is a cross-section of the intermediate portion 40 defined by a plane that is perpendicular to the longitudinal axis 56. The longitudinal axis 56 of the intermediate or medial portion 40 extends from the transition portion 54 toward the distal portion 38 and is offset from the longitudinal axis 20 of the nail 10. The intermediate portion 40, or at least part of the stem portion 36, is radially offset from the longitudinal axis 20 extending through the passageway 50 in the head portion 34. FIG. 7 illustrates that a portion or part of the outer surface of the intermediate or medial portion 40 and a portion or part of the outer surface of the proximal portion 26 lie in a common plane. For example, as illustrated in FIG. 8, one side of the transition portion 54 includes an inwardly beveled or tapered section while the opposing side is a smooth, continuous extension of the outer surface 28 of the proximal portion to the outer surface of the medial portion, wherein the two surfaces share a common tangent, and may share a common plane or surface. That is the outer surface of one side, the top or upper side in FIG. 5, of the nail has a discontinuity, an inwardly beveled part or portion of the transition portion 54, while the opposite outer surface, on the opposite side or the bottom or lower side of the nail 10 has no irregularity, instead having a shared common surface, between the proximal portion 26, transition portion 54, and medial portion 40, extending parallel to the longitudinal axis 20.

Respective cross sections, taken transverse the longitudinal axis 20, of the proximal portion or section 26 and medial portion 40 are closed shapes that touch internally, with both shapes on the same side of a common tangent. In the exemplary embodiment, respective cross sections are circles with the circumference of each circle having a common tangent point with the smaller circle within the larger, see FIG. 7.

The longitudinal axis 20 of the nail 10 coincides with the passageway 50, including the open-faced channel or groove 74 in the medial portion 40 and the bore or aperture 72 in the distal portion or section 38 of the distal end 18. The passageway 50 in the nail 10 includes three sections, the bore or aperture 70 in the head portion 34, the groove 74 in the medial portion 40, and the bore or aperture 72 in the distal portion 38. The foregoing results in the nail 10 captured at each end, both the proximal end 16 and the distal end 18 secured on and following the guide wire 52.

FIG. 10 illustrates the exemplary embodiment of the nail 10 with the stem portion 36 of the nail 22 extends substantially straight, along parallel to the longitudinal axis 20, with the distal portion 38 of the distal end 18, including the conical tip 60, bent upward, toward the side of the nail having the inwardly beveled or tapered section 58. The bend or offset extending at an angle θ with respect to the longitudinal axis 20. The passageway 50 extends in a straight line or path coinciding with the longitudinal axis 20 of the head portion 34 including the proximal portion or section 26. Because the stem portion is offset from the longitudinal axis 20, the passageway forms a groove 74 in the stem portion. Because the distal portion or section 38 of the stem portion 36, the distal end 18 of the nail, bends upward or toward the longitudinal axis 20, the conical tip 60 intersects the longitudinal axis 20 wherein the passageway 50 forms a bore 72 in the distal end 18 of the nail 10. While the stem portion 36 has a longitudinal axis 56 spaced from the longitudinal axis 20, because the distal end 18 is bent upward, the respective longitudinal axes 20, 56 converge at the distal portion 38 of the distal end 18 wherein instead of the passageway 50 forming a groove 74 on the surface of the distal end or portion, it forms a bore 72 in the distal end 18, in particular the conical tip 60. Because the conical tip 60 is bent upwards, once the passageway 50 forms the bore 72 in the distal portion 38 of the distal end, the sidewall 64 surrounding the bore 72 varies in thickness. The conical tip 60 having a longitudinal axis extending at the angle θ, which differs, is incongruent, with the longitudinal axis of the bore 72 in the distal portion 38. As explained subsequently, this occurs because the conical tip 60 is initially formed tapering inwardly toward the longitudinal axis 20. The distal portion 38 is then bent upwardly until a conical surface 60a of the conical tip 60 is parallel to the longitudinal axis 20.

The nail 10 the head portion 34 and stem portion 36 are cylindrically shaped wherein the respective axes thereof are offset. As illustrated, the respective cylindrically shaped head portion and stem portion 34, 36 are offset, so at least a portion of the outer surface of each cylindrical portion lies in a common plane. While the head portion 34 and stem portion 36 are shown with cylindrical shapes, that is circular cross-sections; other shapes or configurations having cross-sections other than circular are contemplated, the understanding being that the longitudinal axis of at least part of the stem portion 36 is offset from the longitudinal axis of the head portion 34 such that the majority of the body of the stem portion 36 sits or is on one side of the longitudinal axis defined by the centerline of the passageway 50 extending through the head portion 34. As shown in FIG. 7 the centerline of the passageway 50 is the longitudinal axis 20 of the head portion 34 and coincides with the axis of the bore or aperture 70. As illustrated, at least a portion of the longitudinal axis 56 of the stem portion 36 is offset from and as shown spaced below the longitudinal axis 20.

Because at least a portion of the intermediate or medial portion 40 is offset from the longitudinal axis of the passageway 50, the passageway extending past the transition portion 54 results in longitudinally extending open-faced channel or groove 74 on an outer surface of the intermediate or medial portion 40. The term "groove" means a narrow channel or indentation on the surface of a three-dimensional object. The groove has depth and walls that extend in the same direction as the longitudinal axis of the nail 10. The passageway 50 continues as groove 74 from the transition portion 54 to the distal portion 38. At the distal portion 38, the passageway 50 extends through the distal portion 38 as a bore or aperture 72.

The passageway 50 extends from the leading or front edge 24 of the distal end to the trailing or rear edge 22 of the proximal end. The passageway 50 receives insertion and extraction instrumentation, such as a guide wire 52, used to position the nail member 10 within the bone 12. As illustrated in FIG. 9, the guide wire 52 is inserted into the passageway 50, initially into the bore or aperture 72, in the distal end 18 at the leading or front edge 24 of the distal end 18. The bore or aperture 72 cannulates the distal portion 38 of the distal end 18 or of the nail 10 enabling it to accept and follow the guide wire 52. Typically, the leading or front edge 24 of the distal end 18 of the nail member 10 follows the path of the guide wire 52 and is inserted into the bone 12 first.

As the nail 10 is inserted into the bone, the guide wire 52 then travels along the channel or groove 74 and ultimately reaches and enters the bore or aperture 70 in the proximal portion or section 26. As illustrated in FIG. 7 the intermediate or medial portion 40 is offset or sits to one side of the guide wire 52.

Figure 12:
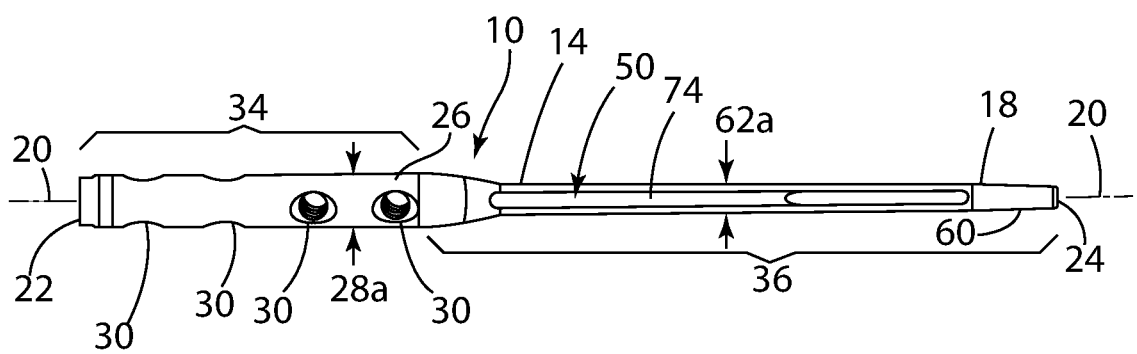
Figure 13:
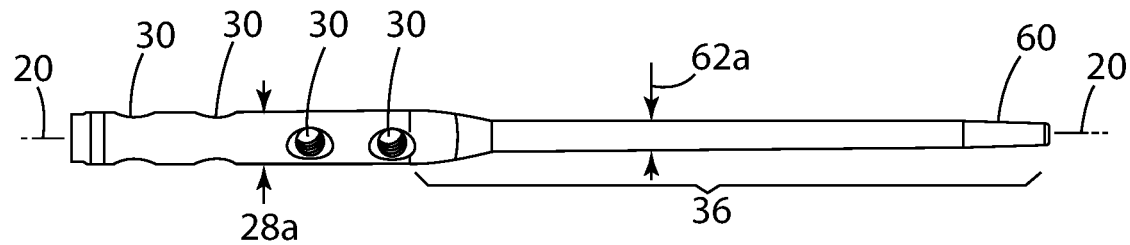

FIGS. 11-13 illustrates an exemplary embodiment of the nail 10 having a degree of curvature such that the distal end 18 of the nail 10 bends upward, or curves inward toward the side having the inwardly beveled or tapered section 58. The longitudinal axis 20 of the nail following the degree of curvature. The degree of curvature providing easy of insertion and stability within the bone.

FIGS. 11-13 illustrate the nail 10 four transverse apertures 34 receiving, as shown in FIG. 2, the two anterior-to-posterior (AP) screws or anchor members 32 received in the fibula 12 and the two syndesmotic screws 44 received in the tibia 13. In the different figures, parts that are equivalent with regard to their function are always provided with the same designations, so the parts are as a rule also described only once.

Figure 14:
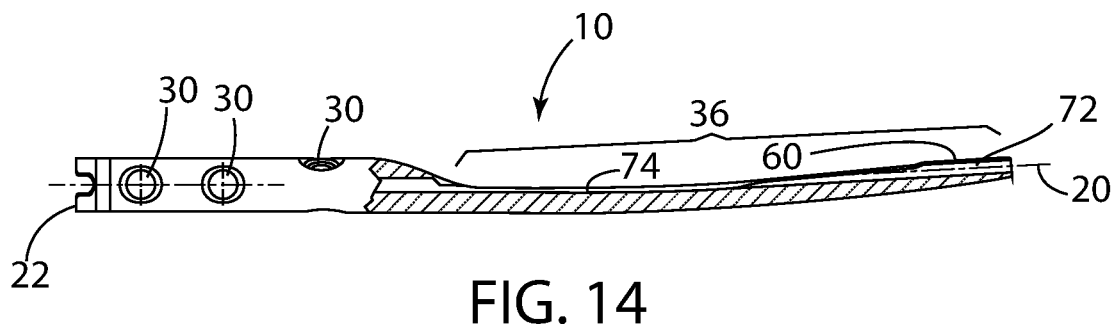
FIGS. 14-16 are a partial cross-sectional side view, top view, and bottom view of an additional embodiment of the nail according to the present invention.
Figure 15:
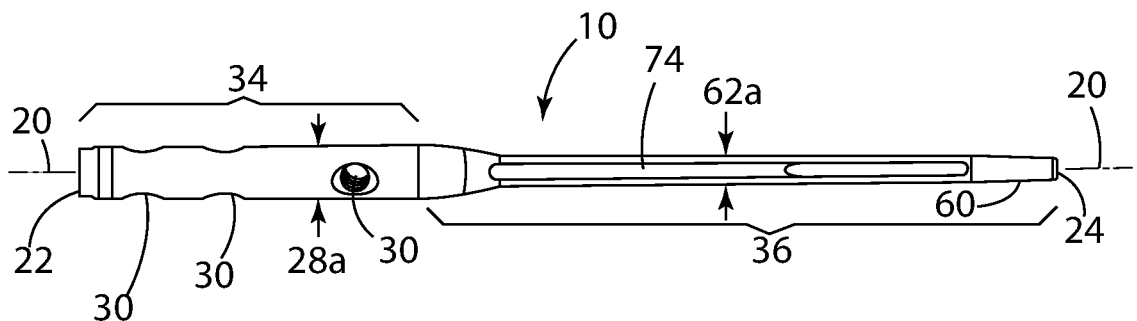
Figure 16:
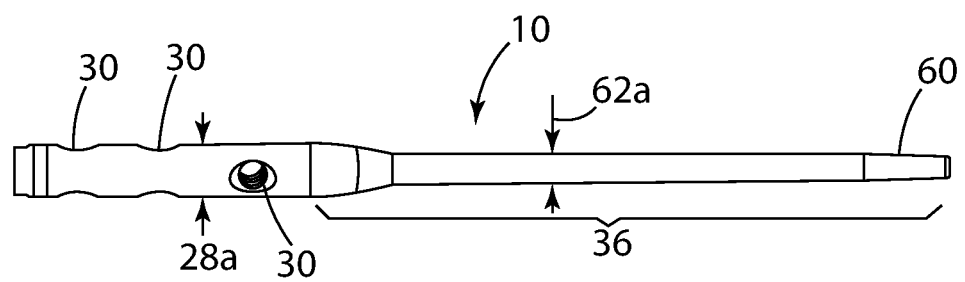

FIGS. 14-16 illustrate the nail 10 having three transverse apertures 30 for receiving, as shown in FIG. 3, the two anterior-to-posterior (AP) screws or anchor members 32 received in the fibula 12 and one syndesmotic screws 44 received in the tibia 13. In the different figures, parts that are equivalent with regard to their function are always provided with the same designations, so the parts are as a rule also described only once.

Figure 17:
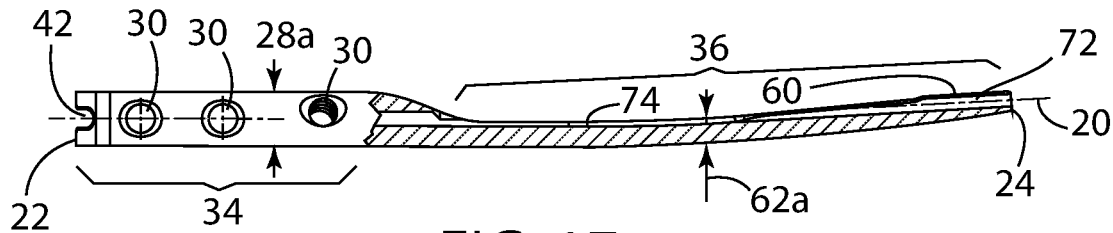
FIGS. 17-19 are a partial cross-sectional side view, top view, and bottom view of a further embodiment of the nail according to the present invention.
Figure 18:
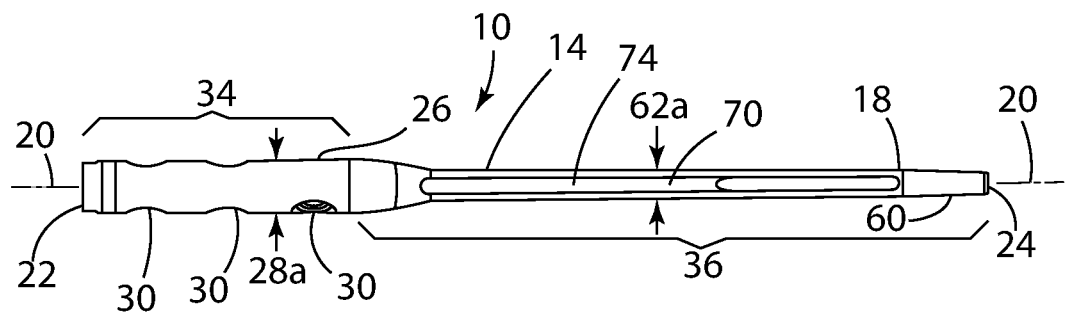
Figure 19:
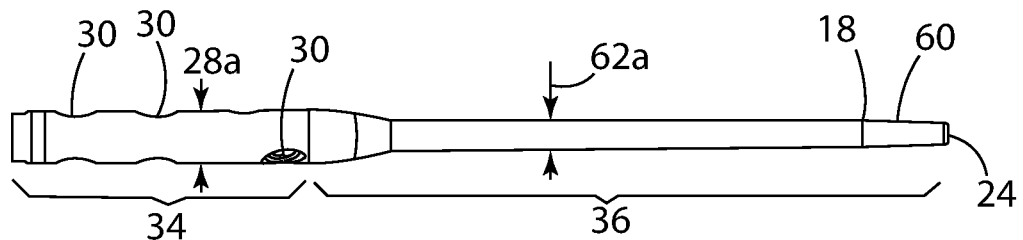

FIGS. 17-19 illustrate the nail 10 having three transverse apertures 30 for receiving, as shown in FIG. 4, the two anterior-to-posterior (AP) screws or anchor members 32 received in the fibula 12 and the one oblique screw 46 also received in the fibula 12, wherein no syndesmotic screws 44 are received in the tibia 13. In the different figures, parts that are equivalent with regard to their function are always provided with the same designations, so the parts are as a rule also described only once.

FIGS. 20-24 and 20a-24a schematically illustrate a manufacturing process for making the nail 10. FIGS. 20 and 20a illustrates that the process starts with machining a symmetrical nail; i.e., the nail 10 is symmetrical about its longitudinal axis 20. Specifically, the nail 10 includes a cylindrical proximal portion 26, a conical transition portion 54 and a cylindrical intermediate or medial portion 40 along with a cylindrical distal portion 38. In another example or embodiment, the nail 10 starts with a cylindrical head portion 34, conical transition portion 54 and cylindrical stem portion 36. All three have a common longitudinal axis, that is a common centerline.

FIGS. 21 and 21a illustrates the next step which includes bending the stem portion 36 and transition portion 54, at the start or beginning of the transition portion 54, the interface between the head portion 34 and transition portion 54, until an outer surface 54a of the transition portion 54 lies in a common plane with the outer surface 28 of the head portion 34. FIGS. 22 and 22a show the distal portion 38 extending below, or past the outer surface 28 of the head portion 34.

FIGS. 23 and 23a illustrates the next step wherein the stem portion 36 or shaft is bent upwards, the bend occurring at the start or beginning of the stem portion 36, the interface between the stem portion 36 and the transition portion 54, until an outer surface 62 of the stem portion 36 lies in a common plane with the outer surface 28 of the head portion 34.

FIGS. 24 and 24a illustrates the next step, which is to bend the distal portion 38 at the distal end 18 of the nail 10 upward in the direction of or toward the centerline or longitudinal axis 20 of the head portion 34. FIG. 39e shows the next step wherein the nail 10 including the head portion and stem portion are cannulated or provided with a passageway. The distal portion 38 includes the conical tip 60 which is also cannulated or provided with a passageway or bore, see for example FIG. 10. In a further step, the nail 10 may also include a bend or curvature.

The process provides a nail 10 having a longitudinally extending bore or apertures 70, 72 in the proximate portion 26 and distal portion 38. The longitudinally extending bores or apertures 70, 72 providing structure for placing the nail 10 on the guide wire 52. Only the proximate portion 26 and distal portion 38 have a longitudinally extending bore or aperture 70, 72 forming part of the passageway 50. As shown in FIG. 5 to the extent the passageway 50 extends in the intermediate or medial portion 40 it is only a groove or open-faced channel 74, not a bore or aperture 70, 72.

Depending upon the embodiment, the intermediate or medial portion 40 may not include a groove or open-faced channel 74. Instead, the passageway 50 can extend between the trailing or rear edge 22 through the proximate portion 26 and outside or space from an outer surface 54a of the transition portion 54. In addition, the passageway 50 extends through the distal end 18, or part of the distal portion 38, and the leading or front edge 24 of the distal end 18. Providing a passageway 50 in this manner helps keep the nail 10 on the guide wire 52 during insertion.

Following are various embodiments or examples of nails 10 using the foregoing inventive concepts, including providing a groove or open-faced channel 74 and an outer surface of the intermediate or medial portion 40. Cannulating or providing the proximal and distal ends 16, 18 with bores or apertures 70, 72 maintains a proper positional relationship of the nail 10 along the guide wire 52 and correspondingly in the bone.

The description of the invention is merely exemplary in nature and, thus, variations that do not depart from the gist of the invention are intended to be within the scope of the invention. Such variations are not to be regarded as a departure from the spirit and scope of the invention.

What is claimed is:

1. A bone nail comprising:
an elongated body having a proximal end and a distal end, the elongated body extending between a rear edge of the proximal end and a front edge of the distal end;
a cylindrical shaped proximal portion at the proximal end, the proximal portion having an outer diameter and a proximal outer surface, the proximal portion including a transverse bore for receiving an anchor member;
a medial portion having a crescent shape and having a medial longitudinal axis, a groove, and a medial outer surface, the medial portion defined by a first arc defined by the groove having a first radius and a second arc defined by the medial outer surface having a second radius different than the first radius, wherein the crescent shape is a cross-section of the medial portion defined by a plane that is perpendicular to the medial longitudinal axis;
the proximal portion including a proximal longitudinal bore extending longitudinally through the proximal portion from the rear edge and communicating with the groove in the medial portion, wherein the proximal longitudinal bore has a proximal longitudinal axis;
the distal end including a distal portion, the distal portion having a distal longitudinal bore extending from the front edge to the groove; and
the medial longitudinal axis of the medial portion offset from the proximal longitudinal axis of the proximal longitudinal bore such that a majority of the medial portion of the elongated body lies on one side of the proximal longitudinal axis of the proximal longitudinal bore, and the proximal outer surface of the proximal portion and the medial outer surface of the medial portion touch a common tangent.

2. The bone nail of claim 1, wherein the distal longitudinal bore in the distal portion has a distal longitudinal axis, and another distal longitudinal axis of the distal portion is incongruent with the distal longitudinal axis of the distal longitudinal bore in the distal portion.

3. The bone nail of claim 1, wherein the distal portion of the distal end has a sidewall circumscribing the distal longitudinal bore in the distal portion, and the distal sidewall varies in thickness.

4. The bone nail of claim 1, wherein the proximal longitudinal bore extending longitudinally through the proximal portion, the groove in the medial portion, and the distal longitudinal bore in the distal portion cooperate to form a continuous passageway extending from the rear edge to the front edge, and the continuous passageway has a single longitudinal axis.

5. The bone nail of claim 4, wherein the single longitudinal axis of the continuous passageway is arcuate.

6. The bone nail of claim 4, wherein the groove in the medial portion has a semi-circular shape.

7. The bone nail of claim 1, wherein the proximal longitudinal axis of the proximal longitudinal bore extending longitudinally through the proximal portion is coincident with the distal longitudinal axis of the distal longitudinal bore in the distal portion.

8. The bone nail of claim 1, wherein the proximal longitudinal bore, the groove in the medial portion, and the distal longitudinal bore in the distal portion cooperate to form a continuous passageway having a single, arcuate longitudinal axis that extends from the rear edge to the front edge, the distal portion of the distal end has a sidewall circumscribing the distal longitudinal bore in the distal portion, and the sidewall varies in thickness.

* * * * *